… …

United States Patent [19]

Enomoto et al.

[11] Patent Number: 5,280,010

[45] Date of Patent: Jan. 18, 1994

[54] AMINO URACIL DERIVATIVES, AND THEIR PRODUCTION AND USE

[75] Inventors: Masayuki Enomoto, Nishinomiya; Susumu Takemura, Takarazuka; Masaharu Sakaki, Toyonaka; Shinsuke Shojima, Takarazuka; Eiki Nagano, Itami, all of Japan

[73] Assignee: Sumitomo Chemical Company, Limited, Osaka, Japan

[21] Appl. No.: 894,606

[22] Filed: Jun. 5, 1992

[30] Foreign Application Priority Data

Jun. 7, 1991 [JP] Japan .................................. 3-136383
Jun. 10, 1991 [JP] Japan .................................. 3-137677

[51] Int. Cl.$^5$ .................... C07D 239/54; A01N 37/32
[52] U.S. Cl. ................................... 504/243; 544/312
[58] Field of Search ........................... 544/312; 71/92; 504/243

[56] References Cited

U.S. PATENT DOCUMENTS

| | | | |
|---|---|---|---|
| 3,920,653 | 11/1975 | Wenzelburger et al. | 71/92 |
| 4,006,008 | 2/1977 | Jager et al. | 71/88 |
| 4,812,164 | 3/1989 | Wenger, II et al. | 71/92 |
| 4,859,229 | 8/1989 | Wenger et al. | 71/92 |
| 5,169,431 | 12/1992 | Enomoto et al. | 504/243 |

FOREIGN PATENT DOCUMENTS 476697  3/1992  European Pat. Off. .

Primary Examiner—Mark L. Berch
Assistant Examiner—P. K. Sripada
Attorney, Agent, or Firm—Birch, Stewart, Kolasch & Birch

[57] ABSTRACT

A compound of the formula:

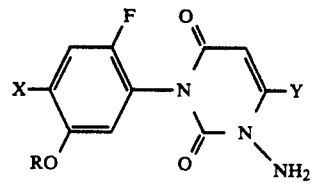

wherein R is lower alkyl, lower alkenyl, lower alkynyl, lower alkoxy(lower)alkyl, halo(lower)alkyl or halo(lower) alkenyl, X is chlorine or bromine, and Y is methyl optionally substituted with halogen, which is useful as an active ingredient of herbicides.

22 Claims, No Drawings

: :
AMINO URACIL DERIVATIVES, AND THEIR PRODUCTION AND USE

FIELD OF THE INVENTION

The present invention relates to novel N-amino uracil derivatives, a process for producing these derivatives, and herbicidal compositions containing the derivatives as an active ingredient.

BACKGROUND OF THE INVENTION

It has hitherto been known that particular kinds of uracil derivatives have herbicidal activity, and there are commercially available herbicides containing such uracil derivatives, for example, under the common name "BROMACIL". U.S. Pat. Nos. 3,920,653 and 4,859,229 disclose some amino uracil and phenyl uracil derivatives, respectively, both of which can be used as an active ingredient of herbicides.

DETAILED DESCRIPTION OF THE INVENTION

The present inventors have intensively studied various compounds and found that N-amino uracil derivatives having a phenyl group with particular substituents have excellent advantages of exhibiting sufficient herbicidal activity and selectivity between crop plants and weeds.

The present invention provides N-amino uracil derivatives of the formula:

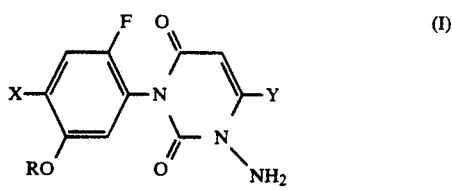

wherein R is lower alkyl, lower alkenyl, lower alkynyl, lower alkoxy(lower)alkyl, halo(lower)alkyl or halo(lower)alkenyl; X is chlorine or bromine; and Y is methyl optionally substituted with halogen.

There is also provided a process for producing the amino uracil derivatives, which comprises reacting a compound of the formula:

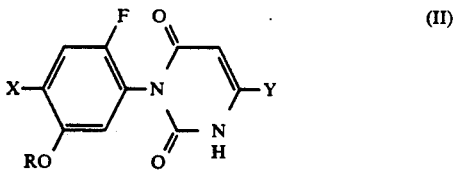

wherein R, X and Y are each as defined above with an aminating agent.

There is also provided a herbicidal composition comprising as an active ingredient the above amino uracil derivatives.

In the amino uracil derivatives (I) of the present invention, examples of the lower alkyl include $C_1$–$C_6$ alkyl. Examples of the lower alkenyl include $C_3$–$C_6$ alkenyl. Examples of the lower alkynyl include $C_3$–$C_6$ alkynyl. Examples of the lower alkoxy(lower)alkyl include $C_1$–$C_4$ alkoxy($C_1$–$C_3$)alkyl. Examples of the halo(lower)alkyl include halo($C_1$–$C_5$)alkyl. Examples of the halo(lower)alkenyl include halo($C_3$–$C_5$)alkenyl.

Examples of the methyl optionally substituted with halogen include methyl and halomethyl.

Among the compounds of the present invention, preferred in view of herbicidal activity are those wherein Y is halomethyl. More preferred are those wherein Y is halomethyl and R is $C_1$–$C_4$ alkyl, $C_3$–$C_4$ alkenyl, $C_3$–$C_4$ alkynyl, $C_1$–$C_4$ alkoxymethyl, or fluoroethyl. Particularly preferred are those wherein Y is trifluoromethyl or difluorochloromethyl and R is $C_1$–$C_4$ alkyl, $C_3$–$C_4$ alkenyl, $C_3$–$C_4$ alkynyl, $C_1$–$C_3$ alkoxymethyl, or 2-fluoroethyl.

Typical examples of the preferred compounds are 1-amino-3-(4-chloro-2-fluoro-5-propargyloxyphenyl)-6-trifluoromethyl-1,2,3,4-tetrahydropyrimidine-2,4-dione, 1-amino-3-[4-chloro-2-fluoro-5-(1-methylpropargyloxy)phenyl]-6-trifluoromethyl-1,2,3,4-tetrahydropyrimidine-2,4-dione, 1-amino-3-[4-chloro-2-fluoro-5-(1-methylethoxy)phenyl]-6-trifluormethyl-1,2,3,4-tetrahydropyrimidine-2,4-dione, and 1-amino-3-[4-chloro-2-fluoro-5-(2-propenyloxy)phenyl]-6-trifluoromethyl-1,2,3,4-tetrahydropyrimidine-2,4-dione.

The compounds of the present invention can be produced by amination of uracil derivatives of the formula:

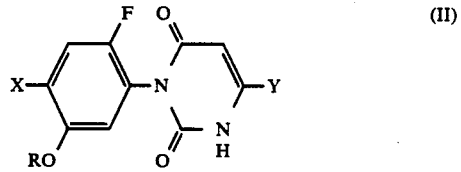

wherein R, X and Y are each as defined above with an aminating agent.

This reaction is usually carried out in a solvent at a temperature of about 0° to 100° C. for a period of 0.5 to 20 hours in the presence of an appropriate base. The aminating agent and the base are used in their respective amounts of 1 to 5 equivalents to one equivalent of the compound (II).

Examples of the solvent include aliphatic hydrocarbons, such as hexane, heptane, ligroin, and petroleum ether; aromatic hydrocarbons, such as benzene, toluene, and xylene; halogenated hydrocarbons, such as chloroform, carbon tetrachloride, dichloroethane, chlorobenzene, and dichlorobenzene; ethers, such as diethyl ether, diisopropyl ether, dioxane, tetrahydrofuran, and diethylene glycol dimethyl ether; ketones, such as acetone, methyl ethyl ketone, methyl isobutyl ketone, isophorone, and cyclohexanone; esters, such as ethyl formate, ethyl acetate, butyl acetate, and diethyl carbonate; tertiary amines, such as pyridine, triethylamine, N,N-diethylaniline, tributylamine, and N-methylmorpholine; acid amides, such as N,N-dimethylformamide and N,N-dimethylacetamide; sulfur compounds, such as dimethylsulfoxide and sulfolane; and liquid ammnonia and water. These solvents may be used solely or in combination.

As the base, there may be used an organic base, such as pyridine, triethylamine, and N,N-diethylaniline; an inorganic base, such as sodium hydroxide, potassium hydroxide, sodium carbonate, potassium carbonate, and sodium hydride; or an alkali metal alkoxide, such as sodium methoxide and sodium ethoxide. Examples of the aminating agent include 2,4-dinitrophenoxyamine, O-mesitylenesulfonylhydroxylamine and hydroxyamine-O-sulfonate.

After completion of the reaction, the reaction mixture is subjected to ordinary post-treatment. For example, the reaction mixture is poured into water, and the precipitated crystals are collected by filtration or extracted with an organic solvent, followed by concentration. If necessary, the product thus obtained may be purified by any conventional procedure, such as chromatography or recrystallization, to give the objective compound of the present invention.

The compound (II), which is the starting compound for the compounds of the present invention, can be produced by the method as disclosed in U.S. Pat. No. 4,859,229.

Various compounds which can be produced according to the above production process are shown in Table 1.

TABLE 1

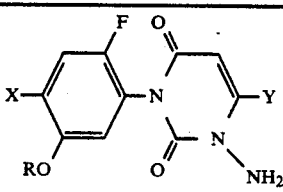

| R | X | Y |
|---|---|---|
| $CH_3$ | Cl | $CF_3$ |
| $C_2H_5$ | Cl | $CF_3$ |
| $n-C_3H_7$ | Cl | $CF_3$ |
| $i-C_3H_7$ | Cl | $CF_3$ |
| $n-C_4H_9$ | Cl | $CF_3$ |
| $i-C_4H_9$ | Cl | $CF_3$ |
| $s-C_4H_9$ | Cl | $CF_3$ |
| $C_5H_{11}$ | Cl | $CF_3$ |
| $C_6H_{13}$ | Cl | $CF_3$ |
| $CH_2OCH_3$ | Cl | $CF_3$ |
| $CH(CH_3)OCH_3$ | Cl | $CF_3$ |
| $CH_2OC_2H_5$ | Cl | $CF_3$ |
| $CH(CH_3)OC_2H_5$ | Cl | $CF_3$ |
| $CH_2OC_3H_7$ | Cl | $CF_3$ |
| $CH(CH_3)OC_3H_7$ | Cl | $CF_3$ |
| $CH_2OC_4H_9$ | Cl | $CF_3$ |
| $CH(CH_3)OC_4H_9$ | Cl | $CF_3$ |
| $CH_3$ | Br | $CF_3$ |
| $C_2H_5$ | Br | $CF_3$ |
| $n-C_3H_7$ | Br | $CF_3$ |
| $i-C_3H_7$ | Br | $CF_3$ |
| $n-C_4H_9$ | Br | $CF_3$ |
| $i-C_4H_9$ | Br | $CF_3$ |
| $s-C_4H_9$ | Br | $CF_3$ |
| $C_5H_{11}$ | Br | $CF_3$ |
| $C_6H_{13}$ | Br | $CF_3$ |
| $CH_2OCH_3$ | Br | $CF_3$ |
| $CH(CH_3)OCH_3$ | Br | $CF_3$ |
| $CH_2OC_2H_5$ | Br | $CF_3$ |
| $CH(CH_3)OC_2H_5$ | Br | $CF_3$ |
| $CH_2OC_3H_7$ | Br | $CF_3$ |
| $CH(CH_3)OC_3H_7$ | Br | $CF_3$ |
| $CH_2OC_4H_9$ | Br | $CF_3$ |
| $CH(CH_3)OC_4H_9$ | Br | $CF_3$ |
| $CH_2CH=CH_2$ | Cl | $CF_3$ |
| $CH(CH_3)CH=CH_2$ | Cl | $CF_3$ |
| $CH_2CH=CHCH_3$ | Cl | $CF_3$ |
| $CH(CH_3)CH=CHCH_3$ | Cl | $CF_3$ |
| $CH_2CH=C(CH_3)_2$ | Cl | $CF_3$ |
| $CH(CH_3)CH=C(CH_3)_2$ | Cl | $CF_3$ |
| $CH_2C\equiv CH$ | Cl | $CF_3$ |
| $CH(CH_3)C\equiv CH$ | Cl | $CF_3$ |
| $CH_2C\equiv CCH_3$ | Cl | $CF_3$ |
| $CH(CH_3)C\equiv CCH_3$ | Cl | $CF_3$ |
| $CH_2CCl=CH_2$ | Cl | $CF_3$ |
| $CH_2CH=CHCl$ | Cl | $CF_3$ |
| $CH_2CH=CCl_2$ | Cl | $CF_3$ |
| $CH_2CH_2F$ | Cl | $CF_3$ |
| $CH_2CF_3$ | Cl | $CF_3$ |

TABLE 1-continued

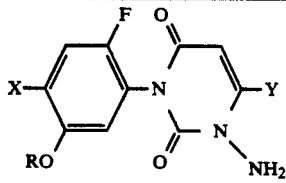

| R | X | Y |
|---|---|---|
| $C_2H_4OCH_3$ | Cl | $CF_3$ |
| $C_2H_4OC_2H_5$ | Cl | $CF_3$ |
| $CH_2CH=CH_2$ | Br | $CF_3$ |
| $CH(CH_3)CH=CH_2$ | Br | $CF_3$ |
| $CH_2CH=CHCH_3$ | Br | $CF_3$ |
| $CH(CH_3)CH=CHCH_3$ | Br | $CF_3$ |
| $CH_2CH=C(CH_3)_2$ | Br | $CF_3$ |
| $CH(CH_3)CH=C(CH_3)_2$ | Br | $CF_3$ |
| $CH_2C\equiv CH$ | Br | $CF_3$ |
| $CH(CH_3)C\equiv CH$ | Br | $CF_3$ |
| $CH_2C\equiv CCH_3$ | Br | $CF_3$ |
| $CH(CH_3)C\equiv CCH_3$ | Br | $CF_3$ |
| $CH_2CCl=CH_2$ | Br | $CF_3$ |
| $CH_2CH=CHCl$ | Br | $CF_3$ |
| $CH_2CH=CCl_2$ | Br | $CF_3$ |
| $CH_2CH_2F$ | Br | $CF_3$ |
| $CH_2CF_3$ | Br | $CF_3$ |
| $C_2H_4OCH_3$ | Br | $CF_3$ |
| $C_2H_4OC_2H_5$ | Br | $CF_3$ |
| $CH_3$ | Cl | $CF_2H$ |
| $C_2H_5$ | Cl | $CF_2H$ |
| $n-C_3H_7$ | Cl | $CF_2H$ |
| $i-C_3H_7$ | Cl | $CF_2H$ |
| $n-C_4H_9$ | Cl | $CF_2H$ |
| $i-C_4H_9$ | Cl | $CF_2H$ |
| $s-C_4H_9$ | Cl | $CF_2H$ |
| $C_5H_{11}$ | Cl | $CF_2H$ |
| $C_6H_{13}$ | Cl | $CF_2H$ |
| $CH_2OCH_3$ | Cl | $CF_2H$ |
| $CH(CH_3)OCH_3$ | Cl | $CF_2H$ |
| $CH_2OC_2H_5$ | Cl | $CF_2H$ |
| $CH(CH_3)OC_2H_5$ | Cl | $CF_2H$ |
| $CH_2OC_3H_7$ | Cl | $CF_2H$ |
| $CH(CH_3)OC_3H_7$ | Cl | $CF_2H$ |
| $CH_2OC_4H_9$ | Cl | $CF_2H$ |
| $CH(CH_3)OC_4H_9$ | Cl | $CF_2H$ |
| $CH_3$ | Br | $CF_2H$ |
| $C_2H_5$ | Br | $CF_2H$ |
| $n-C_3H_7$ | Br | $CF_2H$ |
| $i-C_3H_7$ | Br | $CF_2H$ |
| $n-C_4H_9$ | Br | $CF_2H$ |
| $i-C_4H_9$ | Br | $CF_2H$ |
| $s-C_4H_9$ | Br | $CF_2H$ |
| $C_5H_{11}$ | Br | $CF_2H$ |
| $C_6H_{13}$ | Br | $CF_2H$ |
| $CH_2OCH_3$ | Br | $CF_2H$ |
| $CH(CH_3)OCH_3$ | Br | $CF_2H$ |
| $CH_2OC_2H_5$ | Br | $CF_2H$ |
| $CH(CH_3)OC_2H_5$ | Br | $CF_2H$ |
| $CH_2OC_3H_7$ | Br | $CF_2H$ |
| $CH(CH_3)OC_3H_7$ | Br | $CF_2H$ |
| $CH_2OC_4H_9$ | Br | $CF_2H$ |
| $CH(CH_3)OC_4H_9$ | Br | $CF_2H$ |
| $CH_2CH=CH_2$ | Cl | $CF_2H$ |
| $CH(CH_3)CH=CH_2$ | Cl | $CF_2H$ |
| $CH_2CH=CHCH_3$ | Cl | $CF_2H$ |
| $CH(CH_3)CH=CHCH_3$ | Cl | $CF_2H$ |
| $CH_2CH=C(CH_3)_2$ | Cl | $CF_2H$ |
| $CH(CH_3)CH=C(CH_3)_2$ | Cl | $CF_2H$ |
| $CH_2C\equiv CH$ | Cl | $CF_2H$ |
| $CH(CH_3)C\equiv CH$ | Cl | $CF_2H$ |
| $CH_2C\equiv CCH_3$ | Cl | $CF_2H$ |
| $CH(CH_3)C\equiv CCH_3$ | Cl | $CF_2H$ |
| $CH_2CCl=CH_2$ | Cl | $CF_2H$ |
| $CH_2CH=CHCl$ | Cl | $CF_2H$ |
| $CH_2CH=CCl_2$ | Cl | $CF_2H$ |
| $CH_2CH_2F$ | Cl | $CF_2H$ |
| $CH_2CF_3$ | Cl | $CF_2H$ |
| $C_2H_4OCH_3$ | Cl | $CF_2H$ |
| $C_2H_4OC_2H_5$ | Cl | $CF_2H$ |
| $CH_2CH=CH_2$ | Br | $CF_2H$ |

TABLE 1-continued

| R | X | Y |
|---|---|---|
| CH(CH₃)CH=CH₂ | Br | CF₂H |
| CH₂CH=CHCH₃ | Br | CF₂H |
| CH(CH₃)CH=CHCH₃ | Br | CF₂H |
| CH₂CH=C(CH₃)₂ | Br | CF₂H |
| CH(CH₃)CH=C(CH₃)₂ | Br | CF₂H |
| CH₂C≡CH | Br | CF₂H |
| CH(CH₃)C≡CH | Br | CF₂H |
| CH₂C≡CCH₃ | Br | CF₂H |
| CH(CH₃)C≡CCH₃ | Br | CF₂H |
| CH₂CCl=CH₂ | Br | CF₂H |
| CH₂CH=CHCl | Br | CF₂H |
| CH₂CH=CCl₂ | Br | CF₂H |
| CH₂CH₂F | Br | CF₂H |
| CH₂CF₃ | Br | CF₂H |
| C₂H₄OCH₃ | Br | CF₂H |
| C₂H₄OC₂H₅ | Br | CF₂H |
| CH₃ | Cl | CF₂Cl |
| C₂H₅ | Cl | CF₂Cl |
| n-C₃H₇ | Cl | CF₂Cl |
| i-C₃H₇ | Cl | CF₂Cl |
| n-C₄H₉ | Cl | CF₂Cl |
| i-C₄H₉ | Cl | CF₂Cl |
| s-C₄H₉ | Cl | CF₂Cl |
| C₅H₁₁ | Cl | CF₂Cl |
| C₆H₁₃ | Cl | CF₂Cl |
| CH₂OCH₃ | Cl | CF₂Cl |
| CH(CH₃)OCH₃ | Cl | CF₂Cl |
| CH₂OC₂H₅ | Cl | CF₂Cl |
| CH(CH₃)OC₂H₅ | Cl | CF₂Cl |
| CH₂OC₃H₇ | Cl | CF₂Cl |
| CH(CH₃)OC₃H₇ | Cl | CF₂Cl |
| CH₂OC₄H₉ | Cl | CF₂Cl |
| CH(CH₃)OC₄H₉ | Cl | CF₂Cl |
| CH₃ | Br | CF₂Cl |
| C₂H₅ | Br | CF₂Cl |
| n-C₃H₇ | Br | CF₂Cl |
| i-C₃H₇ | Br | CF₂Cl |
| n-C₄H₉ | Br | CF₂Cl |
| i-C₄H₉ | Br | CF₂Cl |
| s-C₄H₉ | Br | CF₂Cl |
| C₅H₁₁ | Br | CF₂Cl |
| C₆H₁₃ | Br | CF₂Cl |
| CH₂OCH₃ | Br | CF₂Cl |
| CH(CH₃)OCH₃ | Br | CF₂Cl |
| CH₂OC₂H₅ | Br | CF₂Cl |
| CH(CH₃)OC₂H₅ | Br | CF₂Cl |
| CH₂OC₃H₇ | Br | CF₂Cl |
| CH(CH₃)OC₃H₇ | Br | CF₂Cl |
| CH₂OC₄H₉ | Br | CF₂Cl |
| CH(CH₃)OC₄H₉ | Br | CF₂Cl |
| CH₂CH=CH₂ | Cl | CF₂Cl |
| CH(CH₃)CH=CH₂ | Cl | CF₂Cl |
| CH₂CH=CHCH₃ | Cl | CF₂Cl |
| CH(CH₃)CH=CHCH₃ | Cl | CF₂Cl |
| CH₂CH=C(CH₃)₂ | Cl | CF₂Cl |
| CH(CH₃)CH=C(CH₃)₂ | Cl | CF₂Cl |
| CH₂C≡CH | Cl | CF₂Cl |
| CH(CH₃)C≡CH | Cl | CF₂Cl |
| CH₂C≡CCH₃ | Cl | CF₂Cl |
| CH(CH₃)C≡CCH₃ | Cl | CF₂Cl |
| CH₂CCl=CH₂ | Cl | CF₂Cl |
| CH₂CH=CHCl | Cl | CF₂Cl |
| CH₂CH=CCl₂ | Cl | CF₂Cl |
| CH₂CH₂F | Cl | CF₂Cl |
| CH₂CF₃ | Cl | CF₂Cl |
| C₂H₄OCH₃ | Cl | CF₂Cl |
| C₂H₄OC₂H₅ | Cl | CF₂Cl |
| CH₂CH=CH₂ | Br | CF₂Cl |
| CH(CH₃)CH=CH₂ | Br | CF₂Cl |
| CH₂CH=CHCH₃ | Br | CF₂Cl |
| CH(CH₃)CH=CHCH₃ | Br | CF₂Cl |
| CH₂CH=C(CH₃)₂ | Br | CF₂Cl |
| CH(CH₃)CH=C(CH₃)₂ | Br | CF₂Cl |
| CH₂C≡CH | Br | CF₂Cl |
| CH(CH₃)C≡CH | Br | CF₂Cl |
| CH₂C≡CCH₃ | Br | CF₂Cl |
| CH(CH₃)C≡CCH₃ | Br | CF₂Cl |
| CH₂CCl=CH₂ | Br | CF₂Cl |
| CH₂CH=CHCl | Br | CF₂Cl |
| CH₂CH=CCl₂ | Br | CF₂Cl |
| CH₂CH₂F | Br | CF₂Cl |
| CH₂CF₃ | Br | CF₂Cl |
| C₂H₄OCH₃ | Br | CF₂Cl |
| C₂H₄OC₂H₅ | Br | CF₂Cl |
| CH₃ | Cl | CH₃ |
| C₂H₅ | Cl | CH₃ |
| n-C₃H₇ | Cl | CH₃ |
| i-C₃H₇ | Cl | CH₃ |
| n-C₄H₉ | Cl | CH₃ |
| i-C₄H₉ | Cl | CH₃ |
| s-C₄H₉ | Cl | CH₃ |
| C₅H₁₁ | Cl | CH₃ |
| C₆H₁₃ | Cl | CH₃ |
| CH₂OCH₃ | Cl | CH₃ |
| CH(CH₃)OCH₃ | Cl | CH₃ |
| CH₂OC₂H₅ | Cl | CH₃ |
| CH(CH₃)OC₂H₅ | Cl | CH₃ |
| CH₂OC₃H₇ | Cl | CH₃ |
| CH(CH₃)OC₃H₇ | Cl | CH₃ |
| CH₂OC₄H₉ | Cl | CH₃ |
| CH(CH₃)OC₄H₉ | Cl | CH₃ |
| CH₃ | Br | CH₃ |
| C₂H₅ | Br | CH₃ |
| n-C₃H₇ | Br | CH₃ |
| i-C₃H₇ | Br | CH₃ |
| n-C₄H₉ | Br | CH₃ |
| i-C₄H₉ | Br | CH₃ |
| s-C₄H₉ | Br | CH₃ |
| C₅H₁₁ | Br | CH₃ |
| C₆H₁₃ | Br | CH₃ |
| CH₂OCH₃ | Br | CH₃ |
| CH(CH₃)OCH₃ | Br | CH₃ |
| CH₂OC₂H₅ | Br | CH₃ |
| CH(CH₃)OC₂H₅ | Br | CH₃ |
| CH₂OC₃H₇ | Br | CH₃ |
| CH(CH₃)OC₃H₇ | Br | CH₃ |
| CH₂OC₄H₉ | Br | CH₃ |
| CH(CH₃)OC₄H₉ | Br | CH₃ |
| CH₂CH=CH₂ | Cl | CH₃ |
| CH(CH₃)CH=CH₂ | Cl | CH₃ |
| CH₂CH=CHCH₃ | Cl | CH₃ |
| CH(CH₃)CH=CHCH₃ | Cl | CH₃ |
| CH₂CH=C(CH₃)₂ | Cl | CH₃ |
| CH(CH₃)CH=C(CH₃)₂ | Cl | CH₃ |
| CH₂C≡CH | Cl | CH₃ |
| CH(CH₃)C≡CH | Cl | CH₃ |
| CH₂C≡CCH₃ | Cl | CH₃ |
| CH(CH₃)C≡CCH₃ | Cl | CH₃ |
| CH₂CCl=CH₂ | Cl | CH₃ |
| CH₂CH=CHCl | Cl | CH₃ |
| CH₂CH=CCl₂ | Cl | CH₃ |
| CH₂CH₂F | Cl | CH₃ |
| CH₂CF₃ | Cl | CH₃ |
| C₂H₄OCH₃ | Cl | CH₃ |
| C₂H₄OC₂H₅ | Cl | CH₃ |
| CH₂CH=CH₂ | Br | CH₃ |
| CH(CH₃)CH=CH₂ | Br | CH₃ |
| CH₂CH=CHCH₃ | Br | CH₃ |
| CH(CH₃)CH=CHCH₃ | Br | CH₃ |
| CH₂CH=C(CH₃)₂ | Br | CH₃ |
| CH(CH₃)CH=C(CH₃)₂ | Br | CH₃ |
| CH₂C≡CH | Br | CH₃ |

TABLE 1-continued

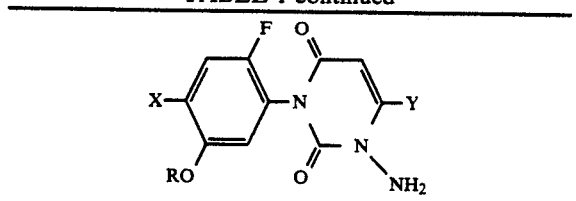

| R | X | Y |
|---|---|---|
| CH(CH₃)C≡CH | Br | CH₃ |
| CH₂C≡CCH₃ | Br | CH₃ |
| CH(CH₃)C≡CCH₃ | Br | CH₃ |
| CH₂CCl=CH₂ | Br | CH₃ |
| CH₂CH=CHCl | Br | CH₃ |
| CH₂CH=CCl₂ | Br | CH₃ |
| CH₂CH₂F | Br | CH₃ |
| CH₂CF₃ | Br | CH₃ |
| C₂H₄OCH₃ | Br | CH₃ |
| C₂H₄OC₂H₅ | Br | CH₃ |
| CH₃ | Cl | CF₂Br |
| C₂H₅ | Cl | CF₂Br |
| n-C₃H₇ | Cl | CF₂Br |
| i-C₃H₇ | Cl | CF₂Br |
| n-C₄H₉ | Cl | CF₂Br |
| i-C₄H₉ | Cl | CF₂Br |
| s-C₄H₉ | Cl | CF₂Br |
| C₅H₁₁ | Cl | CF₂Br |
| C₆H₁₃ | Cl | CF₂Br |
| CH₂OCH₃ | Cl | CF₂Br |
| CH(CH₃)OCH₃ | Cl | CF₂Br |
| CH₂OC₂H₅ | Cl | CF₂Br |
| CH(CH₃)OC₂H₅ | Cl | CF₂Br |
| CH₂OC₃H₇ | Cl | CF₂Br |
| CH(CH₃)OC₃H₇ | Cl | CF₂Br |
| CH₂OC₄H₉ | Cl | CF₂Br |
| CH(CH₃)OC₄H₉ | Cl | CF₂Br |
| CH₃ | Br | CF₂Br |
| C₂H₅ | Br | CF₂Br |
| n-C₃H₇ | Br | CF₂Br |
| i-C₃H₇ | Br | CF₂Br |
| n-C₄H₉ | Br | CF₂Br |
| i-C₄H₉ | Br | CF₂Br |
| s-C₄H₉ | Br | CF₂Br |
| C₅H₁₁ | Br | CF₂Br |
| C₆H₁₃ | Br | CF₂Br |
| CH₂OCH₃ | Br | CF₂Br |
| CH(CH₃)OCH₃ | Br | CF₂Br |
| CH₂OC₂H₅ | Br | CF₂Br |
| CH(CH₃)OC₂H₅ | Br | CF₂Br |
| CH₂OC₃H₇ | Br | CF₂Br |
| CH(CH₃)OC₃H₇ | Br | CF₂Br |
| CH₂OC₄H₉ | Br | CF₂Br |
| CH(CH₃)OC₄H₉ | Br | CF₂Br |
| CH₂CH=CH₂ | Cl | CF₂Br |
| CH(CH₃)CH=CH₂ | Cl | CF₂Br |
| CH₂CH=CHCH₃ | Cl | CF₂Br |
| CH(CH₃)CH=CHCH₃ | Cl | CF₂Br |
| CH₂CH=C(CH₃)₂ | Cl | CF₂Br |
| CH(CH₃)CH=C(CH₃)₂ | Cl | CF₂Br |
| CH₂C≡CH | Cl | CF₂Br |
| CH(CH₃)C≡CH | Cl | CF₂Br |
| CH₂C≡CCH₃ | Cl | CF₂Br |
| CH(CH₃)C≡CCH₃ | Cl | CF₂Br |
| CH₂CCl=CH₂ | Cl | CF₂Br |
| CH₂CH=CHCl | Cl | CF₂Br |
| CH₂CH=CCl₂ | Cl | CF₂Br |
| CH₂CH₂F | Cl | CF₂Br |
| CH₂CF₃ | Cl | CF₂Br |
| C₂H₄OCH₃ | Cl | CF₂Br |
| C₂H₄OC₂H₅ | Cl | CF₂Br |
| CH₂CH=CH₂ | Br | CF₂Br |
| CH(CH₃)CH=CH₂ | Br | CF₂Br |
| CH₂CH=CHCH₃ | Br | CF₂Br |
| CH(CH₃)CH=CHCH₃ | Br | CF₂Br |
| CH₂CH=C(CH₃)₂ | Br | CF₂Br |
| CH(CH₃)CH=C(CH₃)₂ | Br | CF₂Br |
| CH₂C≡CH | Br | CF₂Br |
| CH(CH₃)C≡CH | Br | CF₂Br |
| CH₂C≡CCH₃ | Br | CF₂Br |
| CH(CH₃)C≡CCH₃ | Br | CF₂Br |

TABLE 1-continued

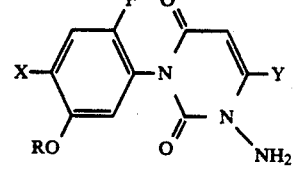

| R | X | Y |
|---|---|---|
| CH₂CCl=CH₂ | Br | CF₂Br |
| CH₂CH=CHCl | Br | CF₂Br |
| CH₂CH=CCl₂ | Br | CF₂Br |
| CH₂CH₂F | Br | CF₂Br |
| CH₂CF₃ | Br | CF₂Br |
| C₂H₄OCH₃ | Br | CF₂Br |
| C₂H₄OC₂H₅ | Br | CF₂Br |

The following examples further illustrate the present invention in detail but are not to be construed to limit the scope thereof.

EXAMPLE 1

3-(4-Chloro-2-fluoro-5-propargyloxy-phenyl)-6-trifluoromethyl-1,2,3,4-tretrahydropyrimidine-2,4-dione (2 g) was added slowly to the suspension of 60% sodium hydride (0.22 g) in N,N-dimethylformamide (10 g) while cooling with ice. To the mixture, 2,4-dinitrophenoxyamine (1.1 g) was slowly added at 5° to 20° C., followed by stirring at room temperature for 3 hours. After completion of the reaction, the reaction mixture was poured into water and extracted with ethyl acetate. The organic layer was washed with water, dried with anhydrous magnesium sulfate and concentrated under reduced pressure. The residue was purified by silica gel chromatography (eluent: mixture of hexane and ethyl acetate) to give a compound of the present invention, i.e., Compound No. 5 (0.9 g).

$^1$H-NMR=$\delta$(ppm) (60 MHz, CDCl₃): 2.54 (1 H, t, J=3 Hz), 4.59 (2 H, bs, NH₂), 4.70 (2 H, d, J=3 Hz), 6.23 (1 H, s), 7.05 (1 H, d, J=6 Hz), 7.16 (1 H, d, J=9 Hz).

EXAMPLE 2

3-[4-Chloro-2-fluoro-5-(1-methylpropargyloxy)-phenyl]-6-methyl-1,2,3,4-tetrahydropyrimidine-2,4-dione (3 g) was added slowly to the suspension of 60% sodium hydride (0.31 g) in N,N-dimethylformamide (10 g) while cooling with ice. To the mixture, 2,4-dinitrophenoxyamine (1.7 g) was slowly added at 5° to 20° C., followed by stirring at room temperature for 3 hours. After completion of the reaction, the reaction mixture was poured into water and extracted with ethyl acetate. The organic layer was washed with water, dried with anhydrous magnesium sulfate and concentrated under reduced pressure. The residue was purified by silica gel chromatography (eluent: mixture of hexane and ethyl acetate) to give a compound of the present invention, i.e., Compound No. 6 (0.9 g).

$^1$H-NMR=$\delta$(ppm) (60 MHz, CDCl₃): 1.65 (3 H, d, J=6 Hz), 2.17 (3 H, s), 2.50 (1 H, d, J=2 Hz), 4.43 (2 H, s, NH₂), 4.74 (1 H, dd, J=2, 6 Hz), 5.53 (1 H, s), 6.97 (1 H, d, J=7 Hz), 7.18 (1 H, d, J=9 Hz).

EXAMPLE 3

A solution of 3-[4-bromo-2-fluoro-5-(2-fluoroethoxy)phenyl]-6-trifluoromethyl-1,2,3,4-tetrahydropyrimidine-2,4-dione (0.4 g) in N,N-dimethylformamide (10 ml) are added dropwise to a suspension of 60% sodium hydride (0.05 g) in N,N-dimethylformamide (10 ml) at 5° to 10° C. The mixture is allowed to stir at 10° to 20° C. for additional 30 minutes. To the mixture, 2,4-dinitrophenoxyamine (0.22 g) is added slowly at 10° to 20° C., followed by stirring at room temperature for one hour. The reaction mixture is poured into ice water and extracted with ethyl acetate. The extract is washed with water, dried with anhydrous magnesium sulfate and concentrated under reduced pressure. The residue is purified by silica gel chromatography to give 1-amino-3-[4-bromo-2-fluoro-5-(2-fluoroethoxy)phenyl]-6-trifluoromethyl-1,2,3,4-tetrahydropyrimidine-2,4-dione.

EXAMPLE 4

A solution of 3-(4-bromo-2-fluoro-5-methoxymethoxyphenyl)-6-trifluoromethyl-1,2,3,4-tetrahydropyrimidine-2,4-dione (0.4 g) in N,N-dimethylformamide (10 ml) are added dropwise to a suspension of 60% sodium hydride (0.05 g) in N,N-dimethylformamide (10 ml) at 5° to 10° C. The mixture is allowed to stir at 10° to 20° C. for additional 30 minutes. To the mixture, 2,4-dinitrophenoxyamine (0.22 g) is added slowly at 10° to 20° C., followed by stirring at room temperature for one hour. The reaction mixture is poured into ice water and extracted with ethyl acetate. The extract is washed with water, dried with anhydrous magnesium sulfate, and concentrated under reduced pressure. The residue is purified by silica gel chromatography to give 1-amino-3-(4-bromo-2-fluoro-5-methoxymethoxyphenyl)-6-trifluoromethyl-1,2,3,4-tretrahydropyrimidine-2,4-dione.

According to the above production process, several different compounds of the present invention were further produced, which are shown in Table 2.

TABLE 2

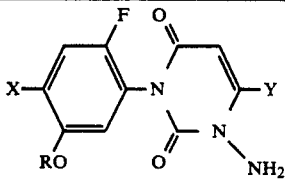

| Compound No. | R | X | Y | Physical property |
|---|---|---|---|---|
| 1 | CH$_3$ | Cl | CF$_3$ | m.p. 176–177° C. |
| 2 | CH$_2$CH=CH$_2$ | Cl | CF$_3$ | m.p. 125–126° C. |
| 3 | i-C$_3$H$_7$ | Cl | CF$_3$ | m.p. 188–189° C. |
| 4 | CH(CH$_3$)C≡CH | Cl | CF$_3$ | m.p. 146–147° C. |
| 5 | CH$_2$C≡CH | Cl | CF$_3$ | resin form |
| 6 | CH(CH$_3$)C≡CH | Cl | CH$_3$ | resin form |
| 7 | CH$_3$ | Cl | CH$_3$ | m.p. 219–220° C. |
| 8 | i-C$_3$H$_7$ | Cl | CF$_2$H | m.p. 218–218.5° C. |
| 9 | i-C$_3$H$_7$ | Cl | CF$_2$Cl | m.p. 176–177° C. |

The compounds of the present invention have high herbicidal activity on a wide variety of weeds including broad-leaved weeds, Graminaceous weeds, Commelinaceous weeds and Cyperaceous weeds in agricultural plowed fields by foliar or soil treatment. Some of the compounds of the present invention do not exhibit any undesirable phytotoxicity on various agricultural crops, such as corn, wheat, barley, rice plant, cotton, and soybean.

Examples of the broad-leaved weeds include wild buckwheat (*Polygonum convolvulus*), pale smartweed (*Polygonum lapathifolium*), common purslane (*Portulaca oleracea*), common chickweed (*Stellaria media*), common lambsquarters (*Chenopodium album*), redroot pigweed (*Amaranthus retroflexus*), radish (*Raphanus sativus*), wild mustard (*Sinapis arvensis*), shepherdspurse (*Capsella bursapastoris*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), purple deadnettle (*Lamium purpureum*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata*), sun spurge (*Euphorbia helioscopia*), spotted spurge (*Euphorbia maculata*), and corn marigold (*Chrysanthemum segetum*).

Examples of Graminaceous weeds include Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), bermudagrass (*Cynodon dactylon*), and giant foxtail (*Setaria faberi*).

Examples of Commelinaceous weeds include asiatic dayflower (*Commelina communis*). Examples of Cyperaceous weeds include rice flatsedge (*Cyperus iria*) and purple nutsedge (*Cyperus rotundus*).

The compounds of the present invention are also effective in exterminating paddy field weeds including Graminaceous weeds, such as barnyardgrass (*Echinochloa oryzicola*); broad-leaved weeds, such as common falsepimpernel (*Lindernia procumbens*), indian toothcup (*Rotala indica*), and waterwort (*Elatine triandra*); Cyperaceous weeds, such as umbrella sedge (*Cyperus difformis*), hardstem bulrush (*Scirpus juncoides*), and needle spikerush (*Eleocharis acicularis*); and others, such as monochoria (*Monochoria vaginalis*) and arrowhead (*Sagittaria pygmaea*), without exhibiting any undesirable phytotoxicity to rice plants on flooding treatment.

In cases where the compounds of the present invention are used as an active ingredient of herbicides, they are usually formulated with conventional solid or liquid carriers, surface active agents, or other auxiliary agents into conventional formulations, such as emulsifiable concentrates, wettable powders, flowables, granules, and water-dispersible granules.

These formulations contain the compounds of the present invention as an active ingredient at a content within the range of 0.02% to 80% by weight, preferably of 0.05% to 70% by weight.

Examples of the solid carrier include fine powders or granules of kaolin clay, attapulgite clay, bentonite, terra alba, pyrophyllite, talc, diatomaceous earth, calcite, walnut shell powders, urea, ammonium sulfate, and synthetic hydrous silicate. Examples of the liquid carrier include aromatic hydrocarbons, such as xylene and methylnaphthalene; alcohols, such as isopropanol, ethylene glycol, and cellosolve; ketones, such as acetone, cyclohexanone, and isophorone; vesitable oils, such as soybean oil and cotton seed oil; and others, such as dimethylsulfoxide, N,N-dimethylformamide, acetonitrile, and water.

The surface active agents used for emulsification, dispersing or spreading may be of any type, for example, either anionic surface active agents, such as alkylsulfates, alkylsulfonates, alkylarylsulfonates, dialkylsulfosuccinates, and phosphates of polyoxyethylenealkylaryl ethers; or non-ionic surface active agents, such as polyoxyethylene alkyl ethers, polyoxyethylene alkylaryl ethers, polyoxyethylene polyoxypropylene block copolymer, sorbitan fatty acid esters, and polyoxyethylene sorbitan fatty acid esters.

Examples of the other auxiliary agents include ligninsulfonates, alginate, polyvinyl alcohol, gum arabic, CMC (carboxymethyl cellulose), and PAP (isopropyl acid phosphate).

The following will describe several formulation examples wherein the compounds of the present invention are designated by the respective compound numbers as shown in Table 2. Unless otherwise indicated, parts are by weight.

FORMULATION EXAMPLE 1

Fifty parts of any one of Compound Nos. 1–4 and 7–9, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Five parts of any one of Compound Nos. 1–9, 14 parts of polyoxyethylenestyrylphenyl ether, 6 parts of calcium dodecylbenzenesulfonate, 25 parts of xylene and 50 parts of cyclohexanone are well mixed to obtain an emulsifiable concentrate.

FORMULATION EXAMPLE 3

Two parts of any one of Compound Nos. 1–9, 1 part of synthetic hydrous silicate, 2 parts of calcium ligninsulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of any one of Compound Nos. 1–4 and 7–9, 3 parts of polyoxyethylene sorbitan monooleate, 3 parts of carboxymethyl cellulose and 69 parts of water are mixed together and the mixture is pulverized until the particle size thereof becomes 5 microns or less to obtain a flowable.

FORMULATION EXAMPLE 5

0.05 parts of any one of Compound Nos. 1–9, 1 part of synthetic hydrous silicate, 2 parts of calcium ligninsulfonate, 30 parts of bentonite and 66.95 parts of kaolin clay are well mixed while being powdered. The mixture is then kneaded with water, granulated and dried to obtain granules.

The compounds of the present invention formulated in any suitable formulation are useful for pre-emergence or post-emergence control of undesired weeds by soil treatment, foliar treatment or flood fallowing treatment. The soil treatment includes application to the soil surface prior to or after planting, incorporation into the soil prior to planting or transplanting, and the like. The foliar treatment may be effected by spraying a herbicidal composition containing the compounds of the present invention over the top of plants. It may also be applied directly to the weeds if care must be taken to keep the chemical off the crop foliage.

The compounds of the present invention may be used together with any other herbicide to improve their herbicidal activity. Further, these compounds may be applied in combination with insecticides, acaricides, nematocides, fungicides, plant growth regulators, fertilizers, soil improvers, and the like.

The compounds of the present invention are useful as an active ingredient of herbicidal composition to be employed for paddy fields, plowed fields, orchards, pasture lands, lawns, forests, non-agricultural fields, and the like.

In cases where the compounds of the present invention are used as an active ingredient of herbicidal composition, the dosage of the compound of the invention may vary depending on the prevailing weather conditions, formulation used, prevailing application timing, mode of application, soil involved, crop and weed species, and the like. Usually, however, the dosage is from about 0.005 to 80 grams, preferably from about 0.01 to 40 grams, of the active ingredient per are. The herbicidal composition thus formulated in the form of an emulsifiable concentrate, water-dispersible granule, wettable powder or flowable may usually be employed by diluting it with water at a volume of about 1 to 10 liters per are, if necessary, with addition of an auxiliary agent, such as a spreading agent. The herbicidal composition formulated in the form of granules may usually be applied as such without dilution.

Examples of the spreading agent include, in addition to the surface active agents as described above, polyoxyethylene resin acid (ester), ligninsulfonate, abietic acid salt, dinaphthylmethanedisulfonate, and paraffin.

The compounds of the present invention can also be used as an active ingredient of harvestaid agents, such as defoliants and desiccants for cotton, potato and the like.

The following test examples indicate that the compounds of the present invention are useful as herbicides. The compounds of the present invention are designated by the respective compound numbers as shown in Table 2, while the compounds used for comparison are designated by the respective compound symbol as shown in Table 3.

TABLE 3

| Compound Symbol | Structure | Remarks |
|---|---|---|
| A | 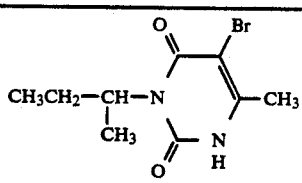 | bromacil |
| B | 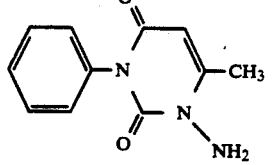 | Compound disclosed in U.S. Pat. No. 3,920,653 |

The herbicidal activity on weeds and phytotoxicity to crop plants are evaluated by visual observation of the degree of inhibition as to the germination and growth of test plants (weeds and crops) used for test, and the results are rated with an index 0, 1, 2, 3, 4 or 5, the numeral "0" indicating that there is no or little difference when compared with the results of untreated plants and the numeral "5" indicating that the test plants are completely dead or the germination or growth of the test plants is completely inhibited.

TEST EXAMPLE 1

Cylindrical plastic pots (diameter, 10 cm; depth, 10 cm) were filled with plowed field soil, and the seeds of Japanese millet, tall morningglory and velvetleaf were sowed therein and covered with soil. The prescribed amount of the test compound which had been formulated in an emulsifiable concentrate as described in Formulation Example 2 was diluted with water, and the dilution was sprayed onto the soil surface by means of a small hand sprayer at a spray volume of 10 liters per are. After the treatment, the test plants were grown in a greenhouse for 19 days, and the herbicidal activity was evaluated. The results are shown in Table 4.

TABLE 4

| Test compound No. | Active ingredient dosage (g/are) | Herbicidal activity | | |
|---|---|---|---|---|
| | | Japanese millet | Tall morning-glory | Velvet-leaf |
| 1 | 5 | 5 | 5 | 5 |
| 2 | 5 | 5 | 5 | 5 |
| 3 | 5 | 5 | 5 | 5 |
| 4 | 5 | 5 | 5 | 5 |
| 5 | 5 | 5 | 5 | 5 |
| 6 | 5 | 5 | 5 | 5 |
| 7 | 5 | 5 | 5 | 5 |
| 8 | 5 | 5 | 5 | 5 |
| 9 | 5 | 5 | 5 | 5 |
| B | 5 | 0 | 0 | 0 |

TEST EXAMPLE 2

Cylindrical plastic pots (diameter, 10 cm; depth, 10 cm) were filled with plowed field soil, and the seeds of tall morningglory and velvetleaf were sowed therein and cultivated in a greenhouse for 10 days. Thereafter, the prescribed amount of the test compound which had been formulated in an emulsifiable concentrate as described in Formulation Example 2 was diluted with water containing a spreading agent, and the dilution was sprayed over the foliage of the test plants by means of a small hand sprayer at a spray volume of 10 liters per are. After the treatment, the test plants were further grown in the greenhouse for 19 days, and the herbicidal activity was evaluated. The results are shown in Table 5.

TABLE 5

| Test compound No. | Active ingredient dosage (g/are) | Herbicidal activity | |
|---|---|---|---|
| | | Tall morning-glory | Velvet-leaf |
| 1 | 0.63 | 5 | 5 |
| 2 | 0.63 | 5 | 5 |
| 3 | 0.63 | 5 | 5 |
| 4 | 0.63 | 5 | 5 |
| 5 | 0.63 | 5 | 5 |
| 6 | 0.63 | 5 | 5 |

TABLE 5-continued

| Test compound No. | Active ingredient dosage (g/are) | Herbicidal activity | |
|---|---|---|---|
| | | Tall morning-glory | Velvet-leaf |
| 7 | 0.63 | 5 | 5 |
| 8 | 0.63 | 5 | 5 |
| 9 | 0.63 | 5 | 5 |
| B | 0.63 | 0 | 0 |

TEST EXAMPLE 3

Cylindrical plastic pots (diameter, 8 cm; depth, 12 cm) were filled with paddy field soil, and the seeds of barnyardgrass, broad-leaved weeds (common falsepimpernel, indian toothcup, waterwort) were sowed therein in 1 to 2 cm depth. After flooding, rice seedlings of 2-leaf stage were transplanted and cultivated in a greenhouse. After 6 days (i.e., at the initial stage of weed emergence), the prescribed amount of the test compound which had been formulated in an emulsifiable concentrate as described in Formulation Example 2 was diluted with water (5 ml), and applied onto the water surface. After the treatment, the test plants were further grown in the greenhouse for 20 days, and the herbicidal activity and phytotoxicity were evaluated. The results are shown in Table 6.

TABLE 6

| Test compound No. | Active ingredient dosage (g/are) | Phyto-toxicity Rice plant | Herbicidal activity | |
|---|---|---|---|---|
| | | | Barnyard-grass | Broad-leaved weeds |
| 3 | 0.16 | 0 | 4 | 5 |
| 4 | 0.63 | 0 | 5 | 5 |
| 5 | 0.16 | 1 | 5 | 5 |
| 6 | 0.16 | 0 | 4 | 5 |
| B | 0.63 | 0 | 0 | 0 |

TEST EXAMPLE 4

Vats (area, 33×23 cm$^2$; depth 11 cm) were filled with plowed field soil, and the seeds of corn, tall morningglory, common cocklebur, velvetleaf, sicklepod, black nightshade and barnyardgrass were sowed therein and cultivated in a greenhouse for 16 days. Thereafter, the prescribed amount of the test compound which had been formulated in an emulsifiable concentrate as described in Formulation Example 2 was diluted with water, and the dilution was uniformly sprayed over the foliage of the test plants by means of a small hand sprayer at a spray volume of 10 liters per are. At this time, the test plants were generally at 1 to 4 leaf stage and in 5 to 30 cm height, although the growing stage of the test plants varied depending on their species. After the treatment, the test plants were further grown in the greenhouse for 18 days, and the herbicidal activity and the phytotoxicity were evaluated. The results are shown in Table 7.

TABLE 7

| Test compound No. | Active ingredient dosage (g/are) | Phyto-toxicity Corn | Herbicidal activity | | | | | |
|---|---|---|---|---|---|---|---|---|
| | | | Tall morning-glory | Common cocklebur | Velvet-leaf | Sicklepod | Black night-shade | Barn-yard-grass |
| 1 | 0.04 | 1 | 5 | 4 | 5 | — | 5 | — |
| 2 | 0.04 | — | 5 | 5 | 5 | 4 | 5 | 4 |
| 3 | 0.04 | 1 | 5 | 5 | 5 | 4 | 5 | 4 |
| 4 | 0.04 | 1 | 5 | 4 | 5 | 4 | 5 | — |
| 5 | 0.04 | 1 | 5 | 5 | 5 | 4 | 5 | 4 |

TABLE 7-continued

| Test compound No. | Active ingredient dosage (g/are) | Phyto- toxicity Corn | Herbicidal activity ||||||
|---|---|---|---|---|---|---|---|---|
| | | | Tall morning- glory | Common cockle- bur | Velvet- leaf | Sickle- pod | Black night- shade | Barn- yard- grass |
| | 0.02 | 1 | 5 | 4 | 5 | — | 5 | — |
| A | 0.04 | 0 | 0 | 0 | 2 | 0 | 3 | 0 |

TEST EXAMPLE 5

Vats (area, 33×23 cm²; depth, 11 cm) were filled with plowed field soil, and the seeds of wheat, pale smartweed, catchweed bedstraw, common chickweed, persian speedwell, field pansy and wild oats were sowed therein and cultivated in a greenhouse for 31 days. Thereafter, the prescribed amount of the test compound which had been formulated in an emulsifiable concentrate as described in Formulation Example 2 was diluted with water, and the dilution was uniformly sprayed over the foliage of the test plants by means of a small hand sprayer at a spray volume of 10 liters per are. At this time, the test plants were generally at 1 to 4 leaf stage and in 3 to 25 cm height, although the growing stage of the test plants varied depending on their species. After the treatment, the test plants were further grown in the greenhouse for 25 days, and the herbicidal activity and phytotoxicity were evaluated. The results are shown in Table 8.

TABLE 8

| Test compound No. | Active ingredient dosage (g/are) | Phyto- toxicity Wheat | Herbicidal activity ||||||
|---|---|---|---|---|---|---|---|---|
| | | | Pale smartweed | Catchweed bedstraw | Common chickweed | Persian speedwell | Field pansy | Wild oats |
| 1 | 0.16 | 1 | 5 | 5 | 5 | 5 | 5 | 4 |
| 2 | 0.16 | 1 | 5 | 5 | 4 | 5 | 5 | 4 |
| 4 | 0.16 | 1 | 5 | 5 | 5 | 5 | 5 | 4 |
| A | 0.16 | 0 | 2 | 2 | 1 | 0 | 0 | 0 |

TEST EXAMPLE 6

Vats (area, 33×23 cm²; depth, 11 cm) were filled with plowed field soil, and the seeds of corn, velvetleaf, black nightshade, Johnsongrass and giant foxtail were sowed therein in 1 to 2 cm depth and covered with soil. The prescribed amount of the test compound which had been formulated in an emulsifiable concentrate as described in Formulation Example 2 was diluted with water, and the dilution was uniformly sprayed onto the soil surface by means of a small had sprayer at a spray volume of 10 liters per are. After the treatment, the test plants were grown in a greenhouse for 18 days, and the herbicidal activity and phytotoxicity were evaluated. The results are shown in Table 9.

TABLE 9

| Test compound No. | Active ingre- dient dosage (g/are) | Phyto- toxicity Corn | Herbicidal activity ||||
|---|---|---|---|---|---|---|
| | | | Velvet- leaf | Black night- shade | Johnson- grass | Giant foxtail |
| 1 | 0.31 | — | 5 | 5 | 5 | 4 |
| 2 | 0.31 | 1 | 5 | 5 | 5 | 5 |
| 3 | 0.31 | — | 5 | 5 | 5 | 5 |
| 4 | 0.31 | 0 | 5 | 5 | 5 | 5 |
| 5 | 0.31 | 0 | 5 | 5 | 5 | 5 |
| A | 0.31 | 0 | 0 | 0 | 0 | 0 |

TEST EXAMPLE 7

Vats (area, 33×23 cm²; depth, 11 cm) were filled with plowed field soil, and the seeds of wheat, barley, pale smartweed, persian speedwell and field pansy were sowed therein in 1 to 2 cm depth and covered with soil. The prescribed amount of the test compound which had been formulated in an emulsifiable concentrate as described in Formulation Example 2 was diluted with water, and the dilution was uniformly sprayed onto the soil surface by means of a small hand sprayer at a spray volume of 10 liters per are. After the treatment, the test plants were grown in a greenhouse for 25 days, and the herbicidal activity and phytotoxicity were evaluated. The results are shown in Table 10.

TABLE 10

| Test com- pound No. | Active ingredient dosage (g/are) | Phytotoxicity ||  Herbicidal activity |||
|---|---|---|---|---|---|---|
| | | Wheat | Barley | Pale smart- weed | Persian speed- well | Field pansy |
| 1 | 0.08 | 1 | — | 4 | — | 5 |
| 2 | 0.16 | 1 | 1 | 5 | 5 | 4 |
| 3 | 0.16 | 0 | 0 | 5 | 5 | — |
| 4 | 0.08 | 1 | 1 | 4 | 5 | 5 |
| 5 | 0.08 | 1 | 1 | 5 | 5 | 5 |
| 6 | 0.63 | 1 | — | 4 | 5 | — |
| 7 | 0.63 | 1 | — | 4 | 5 | 5 |
| B | 0.63 | 0 | 0 | 0 | 0 | 0 |

What is claimed is:

1. A compound of the formula:

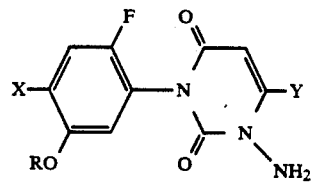

wherein R is lower alkyl, lower alkenyl, lower alkynyl, lower alkoxy(lower)alkyl, halo(lower)alkyl or halo(lower) alkenyl, X is chlorine or bromine, and Y is methyl optionally substituted with halogen.

2. The compound according to claim 1, wherein R is $C_1$-$C_6$ alkyl, $C_3$-$C_6$ alkenyl, $C_3$-$C_6$ alkynyl, $C_1$-$C_4$ alkoxy($C_1$-$C_3$)alkyl, halo($C_1$-$C_5$)alkyl or halo($C_3$-$C_5$)alkenyl.

3. The compound according to claim 1, wherein Y is halomethyl.

4. The compound according to claim 1, wherein Y is methyl.

5. The compound according to claim 1, wherein R is $C_1$-$C_4$ alkyl, $C_3$-$C_4$ alkenyl, $C_3$-$C_4$ alkynyl, $C_1$-$C_4$ alkoxy methyl, or fluoroethyl, and Y is halomethyl.

6. The compound according to claim 1, wherein R is $C_1$-$C_4$ alkyl, $C_3$-$C_4$ alkenyl, $C_3$-$C_4$ alkynyl, $C_1$-$C_3$ alkoxy methyl or 2-fluoroethyl, and Y is trifluoromethyl.

7. The compound according to claim 1, which is 1-amino-3-(4-chloro-2-fluoro-5-propargyloxyphenyl)-6-trifluoromethyl-1,2,3,4-tetrahydropyrimidine-2,4-dione.

8. The compound according to claim 1, which is 1-amino-3-[4-chloro-2-fluoro-5-(1-methylpropargyloxy)phenyl]-6-trifluoromethyl-1,2,3,4tetrahydropyrimidine-2,4-dione.

9. The compound according to claim 1, which is 1-amino-3-[4-chloro-2-fluoro-5-(1-methylethoxy)-phenyl]-6-trifluoromethyl-1,2,3,4-tretrahydropyrimidine-2,4-dione.

10. The compound according to claim 1, which is 1-amino-3-[4-chloro-2-fluoro-5-(2-propenyloxy)-phenyl]-6-trifluoromethyl-1,2,3,4-tetrahydropyrimidine-2,4-dione.

11. A herbicidal composition which comprises as an active ingredient a herbicidally effective amount of the compound according to claim 1, and an inert carrier or diluent.

12. A method for exterminating undesired weeds, which comprises applying a herbicidally effective amount of the compound according to claim 1 and an inert carrier or diluent to the area where the undesired weeds grow or will grow.

13. The compound according to claim 1, wherein X is chlorine or bromine, Y is trifluoromethyl, and R is selected from the group consisting of $CH_3$, $C_2H_5$, n-$C_3H_7$, i-$C_3H_7$, n-$C_4H_9$, i-$C_4H_9$, s-$C_4H_9$, $C_5H_{11}$, $C_6H_{13}$, $CH_2OCH_3$, $CH(CH_3)OCH_3$, $CH_2OC_2H_5$, $CH(CH_3)OC_2H_5$, $CH_2OC_3H_7$, $CH(CH_3)OC_3H_7$, $CH_2OC_4H_9$ and $CH(CH_3)OC_4H_9$.

14. The compound according to claim 1, wherein X is chlorine or bromine, Y is trifluoromethyl, and R is selected from the group consisting of $CH_2CH=CH_2$, $CH(CH_3)CH=CH_2$, $CH_2CH=CHCH_3$, $CH(CH_3)CH=CHCH_3$, $CH_2CH=C(CH_3)_2$, $CH_2C\equiv CH$, $CH(CH_3)C\equiv CH$, $CH_2C\equiv CCH_3$, $CH(CH_3)C\equiv CCH_3$, $CH_2CCl=CH_2$, $CH_2CH=CCl_2$, $CH_2CH_2F$, $CH_2CF_3$, $C_2H_4OCH_3$ and $C_2H_4OC_2H_5$.

15. The compound according to claim 1, wherein X is chlorine or bromine, Y is difluoromethyl, and R is selected from the group consisting of $CH_3$, $C_2H_5$, n-$C_3H_7$, i-$C_3H_7$, n-$C_4H_9$, i-$C_4H_9$, s-$C_4H_9$, $C_5H_{11}$, $C_6H_{13}$, $CH_2OCH_3$, $CH(CH_3)OCH_3$, $CH_2OC_2H_5$, $CH(CH_3)OC_2H_5$, $CH_2OC_3H_7$, $CH(CH_3)OC_3H_7$, $CH_2OC_4H_9$ and $CH(CH_3)OC_4H_9$.

16. The compound according to claim 1, wherein X is chlorine or bromine, Y is difluoromethyl, and R is selected from the group consisting of $CH_2CH=CH_2$, $CH(CH_3)CH=CH_2$, $CH_2CH=CHCH_3$, $CH(CH_3)CH=CHCH_3$, $CH_2CH=C(CH_3)_2$, $CH_2C\equiv CH$, $CH(CH_3)C\equiv CH$, $CH_2C\equiv CCH_3$, $CH(CH_3)C\equiv CCH_3$, $CH_2CCl=CH_2$, $CH_2CH=CCl_2$, $CH_2CH_2F$, $CH_2CF_3$, $C_2H_4OCH_3$ and $C_2H_4OC_2H_5$.

17. The compound according to claim 1, wherein X is chlorine or bromine, Y is difluorochloromethyl, and R is selected from the group consisting of $CH_3$, $C_2H_5$, n-$C_3H_7$, i-$C_3H_7$, n-$C_4H_9$, i-$C_4H_9$, s-$C_4H_9$, $C_5H_{11}$, $C_6H_{13}$, $CH_2OCH_3$, $CH(CH_3)OCH_3$, $CH_2OC_2H_5$, $CH(CH_3)OC_2H_5$, $CH_2OC_3H_7$, $CH(CH_3)OC_3H_7$, $CH_2OC_4H_9$ and $CH(CH_3)OC_4H_9$.

18. The compound according to claim 1, wherein X is chlorine or bromine, Y is difluorochloromethyl, and R is selected from the group consisting of $CH_2CH=CH_2$, $CH(CH_3)CH=CH_2$, $CH_2CH=CHCH_3$, $CH(CH_3)CH=CHCH_3$, $CH_2CH=C(CH_3)_2$, $CH_2C\equiv CH$, $CH(CH_3)C\equiv CH$, $CH_2C\equiv CCH_3$, $CH(CH_3)CH=CCH_3$, $CH_2CCl=CH_2$, $CH_2CH=CCl_2$, $CH_2CH_2F$, $CH_2CF_3$, $C_2H_4OCH_3$ and $C_2H_4OC_2H_5$.

19. The compound according to claim 1, wherein X is chlorine or bromine, Y is methyl, and R is selected from the group consisting of $CH_3$, $C_2H_5$, n-$C_3H_7$, i-$C_3H_7$, n-$C_4H_9$, i-$C_4H_9$, s-$C_4H_9$, $C_5H_{11}$, $C_6H_{13}$, $CH_2OCH_3$, $CH(CH_3)OCH_3$, $CH_2OC_2H_5$, $CH(CH_3)OC_2H_5$, $CH_2OC_3H_7$, $CH(CH_3)OC_3H_7$, $CH_2OC_4H_9$ and $CH(CH_3)OC_4H_9$.

20. The compound according to claim 1 wherein X is chlorine or bromine, Y is methyl, and R is selected from the group consisting of $CH_2CH=CH_2$, $CH(CH_3)CH=CH_2$, $CH_2CH=CHCH_3$, $CH(CH_3)CH=CHCH_3$, $CH_2CH=C(CH_3)_2$, $CH_2C\equiv CH$, $CH(CH_3)C\equiv CH$, $CH_2C\equiv CCH_3$, $CH(CH_3)C\equiv CCH_3$, $CH_2CCl=CH_2$, $CH_2CH=CCl_2$, $CH_2CH_2F$, $CH_2CF_3$, $C_2$, $H_4OCH_3$ and $C_2H_4OC_2H_5$.

21. The compound according to claim 1, wherein X is bromine or chlorine, Y is difluorobromomethyl, and R is selected from the group consisting of $CH_3$, $C_2H_5$, n-$C_3H_7$, i-$C_3H_7$, n-$C_4H_9$, i-$C_4H_9$, s-$C_4H_9$, $C_5H_{11}$, $C_6H_{13}$, $CH_2OCH_3$, $CH(CH_3)OCH_3$, $CH_2OC_2H_5$, $CH(CH_3)OC_2H_5$, $CH_2OC_3H_7$, $CH(CH_3)OC_3H_7$, $CH_2OC_4H_9$ and $CH(CH_3)OC_4H_9$.

22. The compound according to claim 1, wherein X is bromine or chlorine, Y is difluorobromomethyl, and R is selected from the group consisting of $CH_2CH=CH_2$, $CH(CH_3)CH=CH_2$, $CH_2CH=CHCH_3$, $CH(CH_3)CH=CHCH_3$, $CH_2CH=C(CH_3)_2$, $CH_2C\equiv CH$, $CH(CH_3)C\equiv CH$, $CH_2C\equiv CCH_3$, $CH(CH_3)C\equiv CCH_3$, $CH_2CCl=CH_2$, $CH_2CH=CCl_2$, $CH_2CH_2F$, $CH_2CF_3$, $C_2H_4OCH_3$ and $C_2H_4OC_2H_5$.

* * * * *